United States Patent
Tao

(10) Patent No.: US 8,871,927 B2
(45) Date of Patent: Oct. 28, 2014

(54) METHOD FOR PURIFYING CEFTIZOXIME SODIUM

(75) Inventor: Linggang Tao, Wuyi (CN)

(73) Assignee: Hainan Lingkang Pharmaceutical Co., Ltd., Hainan (CN)

( * ) Notice: Subject to any disclaimer, the term of this patent is extended or adjusted under 35 U.S.C. 154(b) by 0 days.

(21) Appl. No.: 14/008,541

(22) PCT Filed: Aug. 11, 2011

(86) PCT No.: PCT/CN2011/001332
§ 371 (c)(1),
(2), (4) Date: Sep. 28, 2013

(87) PCT Pub. No.: WO2013/010297
PCT Pub. Date: Jan. 24, 2013

(65) Prior Publication Data
US 2014/0121369 A1    May 1, 2014

(30) Foreign Application Priority Data
Jul. 15, 2011    (CN) .......................... 2011 1 0197474

(51) Int. Cl.
*C07D 279/00*    (2006.01)
*C07D 501/12*    (2006.01)

(52) U.S. Cl.
CPC .................................. *C07D 501/12* (2013.01)
USPC ........................................................ 544/47

(58) Field of Classification Search
USPC ........................................................ 544/47
See application file for complete search history.

(56) References Cited

FOREIGN PATENT DOCUMENTS

| CN | 101843589 A | 9/2010 |
|---|---|---|
| CN | 102079750 A | 6/2011 |

*Primary Examiner* — T. Victor Oh
(74) *Attorney, Agent, or Firm* — CBM Patent Consulting, LLC

(57) ABSTRACT

A novel process for refining Ceftizoxime sodium compound, comprises the steps of: 1) dissolving crude Ceftizoxime sodium in water, and extracting with cyclohexane or ethyl acetate, followed by separating the organic phase containing impurities, producing an aqueous phase containing Ceftizoxime sodium; 2) adding ammonia or ammonium hydroxide into the above aqueous phase while stirring, followed by filtrating the precipitate, producing an aqueous filtrate containing Ceftizoxime sodium; 3) adding an alcoholic solvent in the aqueous solution and recrystallizing under controlled temperature, followed by centrifuging and washing the resultant crystals, producing the refined Ceftizoxime sodium after drying; and 4) optionally returning the mother liquid of the recrystallization process to step 3).

11 Claims, 1 Drawing Sheet

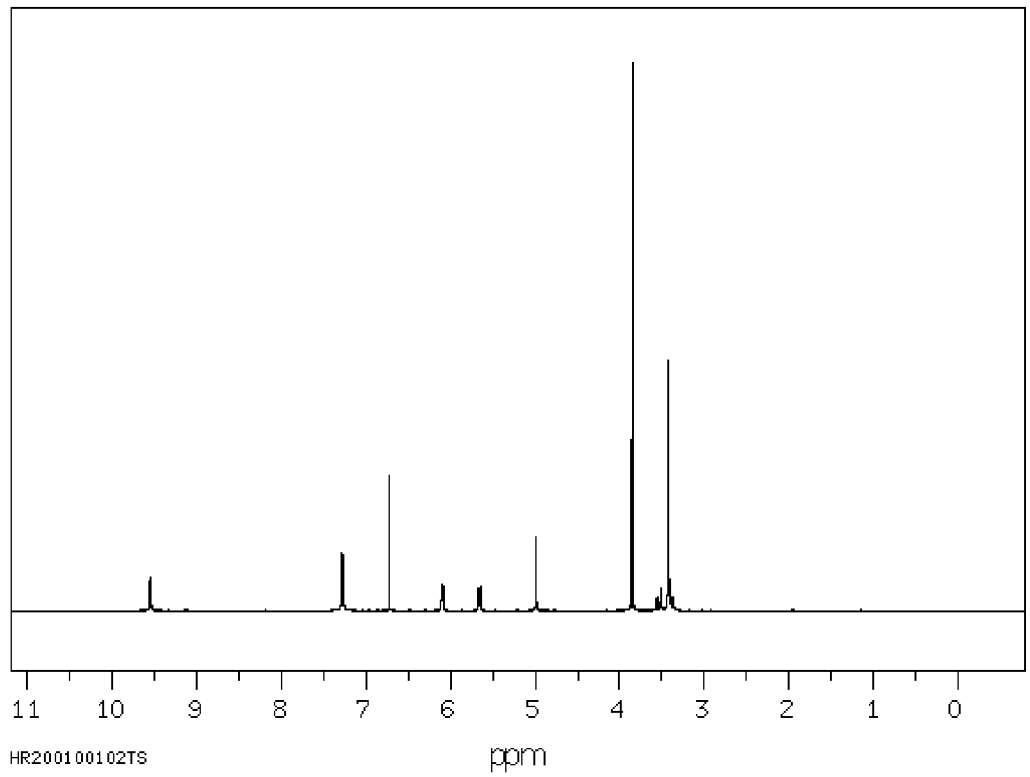
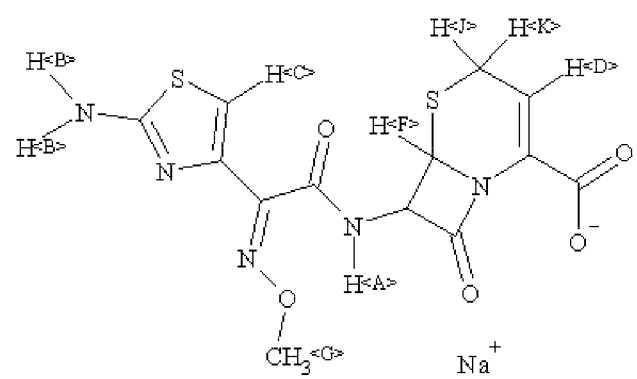
| Assign. | Shift (ppm) |
|---|---|
| A | 9.55 |
| B | 7.27 |
| C | 6.719 |
| D | 6.088 |
| E | 5.65 |
| F | 4.98 |
| G | 3.839 |
| J* | 3.516 |
| K* | 3.4 |

METHOD FOR PURIFYING CEFTIZOXIME SODIUM

FIELD OF THE INVENTION

The present invention relates to Ceftizoxime sodium compound and a novel process for purifying thereof, which belongs to the field of medical technology.

BACKGROUND OF THE INVENTION

Ceftizoxime sodium has a chemical name of sodium (6R, 7R)-7-[2-(2-amino-thiazol-4-yl)-2-methoxyiminoacetylamino]-8-oxo-5-thia-1-azabicyclo[4.2.0]oct-2-ene-2-carboxylic acid with synonyms such as Cefizox. Epocelin and so on. It has a chemical formula of $C_{13}H_{12}N_5NaO_5S_2$ with a molecular weight of 405.38. The content of Ceftizoxime should not less than 85.0% based on anhydrous substances. The structural formula is

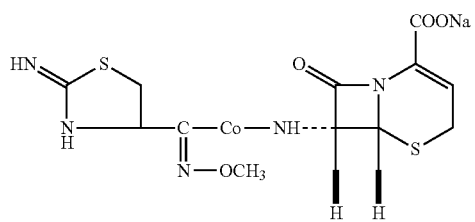

Ceftizoxime sodium is the third-generation cephalosporin with broad-spectrum antibacterial activity and has the stability against broad-spectrum β-lactamases (including Penicillinase and Cephalosporinase) generated by many gram-positive bacteria and gram-negative bacteria. Ceftizoxime sodium has strong antibacterial activity against Enterobacteriaceae bacteria such as *Escherichia coli, Klebsiella pneumoniae*, proteuspneumonia, and *pseudomonas* such as *pseudomonas aeruginosa* and *acinetobacter* is not sensitive to Ceftizoxime sodium. Ceftizoxime sodium has excellent antibacterial activity against *Haemophilus influenzae* and *Neisseria gonorrhoeae*, and is not as good as first- and second-generation cephalosporin in the activity against *Staphyloccocus aureus* Rosenbach and *staphylococcus epidermidis*. The meticillin-resistant-*Staphylococcus aureus* and *enterococcus* are resistant to Ceftizoxime sodium, and verious *Streptococcus* are highly sensitive to Ceftizoxime sodium. Anaerobicbacteria, such as *Peptococcus, Peptostreptococcus* and some *Bacteroides* are sensitive to Ceftizoxime sodium, and *clostridium difficile* is resistant to Ceftizoxime sodium.

The Mechanism of Ceftizoxime sodium lies in that it inhibits biosynthesis of mucopeptide in bacterial cell wall to achieve a bactericidal effect. The indications mainly include infections induced by sensitive bacteria, such as lower respiratory tract infections, urinary tract infections, Abdominal infections, pelvic infections, septicemia, skin and soft tissue infections, bone and joint infections, meningitis and uncomplicated gonorrhea caused by *Streptococcus pneumoniae* or *Haemophilus influenzae*.

A number of references of patents and journals have reported processes for preparing and refining Ceftizoxime sodium.

Chinese patent application CN101671348A reports a process for synthesizing Ceftizoxime sodium, wherein 2-(2-formyl-aminothiazol-4-yl)-2-methoxyimino acetic acid is generated by reaction of Cefotaxime acid and formic acid, which is then reacted with 7-amino-3-none-3-cephem ring-4-carboxylic acid catalyzed by triphenyl phosphine oxide and triphosgene under stirring conditions to form Ceftizoxime sodium, after adjusting the pH value with an acid or a base. However, the yield and the purity of Ceftizoxime sodium prepared by this method are low.

3) The pH value of solution A is adjusted to 0.8~1.2 by hydrochloric acid. Then the solution is filtered and the filtrate is collected to give solution B; 4) The pH value of solution B is adjusted to 1.3~1.75 by a weakly basic solution. After complete crystallization under stirring, the solution is filtered and the resultant crystals are washed with water, to provide the refined Ceftizoxime sodium after vacuum drying. Although the purity of Ceftizoxime sodium is improved by this method, the inherent impurities in the drug substance are difficult to separate by simple reconciling with acids and bases, and additional external impurities may be introduced in the pH adjusting process, active carbon decolorization process and so on, thereby increasing the difficulties in separation.

Currently, Ceftizoxime sodium is manufactured mainly dependent on dispensing from imported raw material drugs by domestic pharmaceutical manufacturers. Although Ceftizoxime sodium is produced in China, however, both the yield and the product purity are still low.

SUMMARY OF THE INVENTION

How to improve the purity of Ceftizoxime sodium is an urgent problem with significant social and economic benefits. To overcome the deficiency of the low purity of Ceftizoxime sodium prepared in the prior art, the present invention provides Ceftizoxime sodium compound and a novel process for refining and purifying thereof.

Ceftizoxime sodium to be refined according to a method of the present invention is Ceftizoxime sodium obtained by currently known synthetic methods, or commercially available or imported Active Pharmaceutical Ingredients of Ceftizoxime sodium, which are collectively referred to as crude or raw Ceftizoxime sodium in the present invention.

After a delicate study, the inventor has found that the purity of crude or raw Ceftizoxime sodium, can be significantly improved by a purification method comprising the following processing steps:

step 1) dissolving crude Ceftizoxime sodium into water, and extracting for several minutes to 10 hours after adding cyclohexane or ethyl acetate, followed by separating the organic phase containing impurities, to provide an aqueous phase containing Ceftizoxime sodium;

step 2) treating for several minutes to 8 hours by adding ammonia or ammonium hydroxide (namely aqueous ammonia) into the above aqueous phase while stirring, followed by filtrating the precipitate, to provide an aqueous filtrate containing Ceftizoxime sodium, optionally the remaining ammonia can be removed by heating;

step 3) adding an alcoholic solvent in the aqueous solution and recrystallizing under controlled temperature, followed by centrifuging and washing the resultant crystals, to provide the refined Ceftizoxime sodium after drying;

step 4) optionally returning the mother liquid of the recrystallization process to step 3), i.e. adding the mother liquid together with the alcoholic solvent in the aqueous solution obtained in step 2).

BRIEF DESCRIPTION OF THE DRAWINGS

FIG. 1 is the $^1$H NMR spectrum of Ceftizoxime sodium prepared in the example 1.

DESCRIPTION OF THE PREFERRED EMBODIMENTS

The steps of a method for purifying Ceftizoxime sodium according to the present invention is detailed hereafter.

step 1) dissolving crude Ceftizoxime sodium into water, and extracting for several minutes to 10 hours after adding cyclohexane or ethyl acetate, followed by separating the organic phase containing impurities, to provide an aqueous phase containing Ceftizoxime sodium.

Generally, the raw Ceftizoxime sodium may contain organic solvents, a variety of raw materials and intermediate products introduced during the preparation. Furthermore, small amount polymers of Ceftizoxime sodium will normally generated during the preparation and the storage, especially at higher temperatures.

The inventors have noted that these substances mainly lead to no high purity of raw Ceftizoxime sodium. They not only reduce the content of active pharmaceutical ingredients, but also deepen the color due to the polymeric impurities. These impurities remain dissolved in the aqueous solution of Ceftizoxime sodium in little amount or in trace amount due to their content are very low.

The inventors found that these impurities general are organic substances, and have a great solubility in organic solvents, especially in cyclohexane or ethyl acetate, which cannot mixed with water. A method for extracting is a normal and effective way of separation. According to the instant invention, after the treatment of step 1), these impurities can be separated from the aqueous solution of Ceftizoxime sodium.

According to a preferred embodiment of the present invention, in step 1), based on the volume, the amount of cyclohexane or ethyl acetate is preferably less than a half of the volume of the aqueous solution of Ceftizoxime sodium, more preferably less than one-third of the volume of the aqueous solution. Extracting may carried out for many times, preferably for 2 to 3 times.

According to a preferred embodiment of the present invention, in step 1), the time for each extracting is preferable from 30 minutes to 8 hours, more preferably from 1 to 6 hours, most preferably from 2 to 4 hours.

According to a preferred embodiment of the present invention, in step 1), stirring is preferable in order to extract fully, and lastly removing the organic phase containing impurities by separating funnel.

step 2) treating for several minutes to 8 hours by adding ammonia or ammonium hydroxide (namely aqueous ammonia) into the above aqueous phase while stirring, followed by filtrating the precipitate, to provide an aqueous filtrate containing Ceftizoxime sodium, optionally the remaining ammonia can be removed by heating.

Without being bound to any theory, the ammonia or ammonium hydroxide treatment is employed in the inventive step 2) to increase the purify for the following reasons:

In general, crude Ceftizoxime sodium also contains a trace of catalyst, salts and heavy metals and other inorganic substances introduced during the preparation, as well as bacterial endotoxins generated during the storage. These substances are generally dissolved in the aqueous solution of Ceftizoxime sodium in trace amount. With the gradual increase of pH due to the ammonium hydroxide added, Cefmenoxime hydrochloride is converted into Cefmenoxime acid and dissolves in aqueous alkaline solution, whereas some inorganic substances are able to form basic salt precipitation and be removed by filtration, thereby effectively reducing the impurities. Through adding ammonia or ammonium hydroxide into the aqueous solution of Ceftizoxime sodium, the solution is adjusted to alkaline, whereas these inorganic substances are able to form basic salt precipitation and be removed by filtration, thereby effectively reducing the impurities.

According to a preferred embodiment of the present invention, ammonia or ammonium hydroxide with a concentration of 15-25% is continuously added into the aqueous phase obtained from step 1), and the treatment time is preferably from 30 minutes to 6 hours, more preferably 1-5 hours, most preferably 2-3 hours, until the pH value of the aqueous solution is from 8 to 11, preferably from 9 to 10. In this treating process, it is under stirring so as to achieve a full mix, and then the precipitation is filtered out.

According to a preferred embodiment of the present invention, the aqueous solution after filtration is heated to 40-90° C., preferably 50-80° C., more preferably 60-70° C., on one hand to remove the remaining ammonia in aqueous solution, and on the other hand to facilitate the subsequent crystallization step.

step 3) adding an alcoholic solvent in the aqueous solution and recrystallizing under controlled temperature, followed by centrifuging and washing the resultant crystals, to provide the refined Ceftizoxime sodium after drying.

It is found in our study that, as for Ceftizoxime sodium, employing refluence and recrystallization in general solvent but for an alcohol as solvent, or suspending in other general solvent and stirring under reflux, it is difficult to well crystallize. Furthermore, it is impossible to achieve expected purity to treat crude Ceftizoxime sodium directly using a separating method with a good-bad solvent.

Ceftizoxime sodium has a great solubility in water, whereas has very small solubility in an alcohol, especially in ethanol as solvent. Therefore, an alcohol, especially ethanol is selected as solvent to recrystallize Ceftizoxime sodium.

Surprisingly, after the inventive treatment of the above steps 1) and 2), by recrystallizing Ceftizoxime sodium with an alcohol, especially ethanol as solvent, very high purity crystals are obtained. The reason may be that the impurities having an adverse effect on the recrystallization have been removed through the inventive steps 1) and 2), and moreover, Ceftizoxime sodium is more suitable for the recrystallization from the aqueous solution of Ceftizoxime sodium with an alcohol as solvent after treating with ammonia or ammonium hydroxide.

According to a preferred embodiment of the present invention, during the recrystallization, firstly, at elevated temperature, such as at 40-90° C., preferably 50-80° C., more preferably 60-70° C., the aqueous solution of Ceftizoxime sodium obtained from step 2) is concentrated in order to the water amount is reduced, and then ethanol with a concentration of 75% bis to absolute ethanol in a volume ratio of 50%-70% based on the aqueous solution is added into the aqueous solution. The temperature is gradually cooled down to a minimum of 10° C., preferably a minimum of 12° C., more preferably a minimum of 15° C., while crystals gradually precipitate.

Generally, the more the temperature drops, the more Ceftizoxime sodium precipitates, but the inventors found that below 10° C., Ceftizoxime sodium tends to precipitate in a form of powder rather than crystals and carry more solvents or impurities.

Ceftizoxime sodium seeds are optionally added in the cooling process.

The crystallization is complete after standing still for 2-24 hours, and then drying such as air drying or drying in an oven is used.

According to a preferred embodiment of the present invention, concentration of the aqueous Ceftizoxime sodium solution can be done while the aqueous solution is heated to remove the remaining ammonia in the step 2), that is, the final heating of the aqueous solution in the step 2), on one hand removes the remaining ammonia, and on the other hand facilitates concentration of the aqueous Ceftizoxime sodium solution. As a result, the crystallization process of the step 3) can proceed directly without cooling.

step 4) optionally returning the mother liquid of the recrystallization process to step 3), i.e. adding the mother liquid together with the alcoholic solvent in the aqueous solution obtained in step 2).

As the crystallization mother liquor is obtained in the step 3) by precipitation after cooling gradually down to a minimum of 10° C., preferably a minimum of 12° C., more preferably a minimum of 15° C., it contains a certain amount of Ceftizoxime sodium which has not precipitated. The crystallization mother liquor is subjected to the step 3) once more, namely, it is added to the aqueous solution together with the alcohol solvent obtained from step 2), to allow crystallization again, improving the yield of Cefmenoxime hydrochloride greatly.

As measured by High Performance Liquid Chromatography (Chinese Pharmacopoeia 2000 Edition, Volume II, Appendix VD), the refined Ceftizoxime sodium obtained according to the above embodiments has a content of Ceftizoxim is not less than 94.00%, and usually not less than 94.10%. The color is white.

In view of the great impact of the powder flowability, intrinsic dissolution rate, solid stability and preparation operability of Ceftizoxime sodium on the activity exhibited and the preparation formulated, a great improvement in the purity of Ceftizoxime sodium would improve substantially the dissolution rate, the formulatability and the stability.

Therefore, the refined Ceftizoxime sodium according to a purification method of the present invention is well suitable for preparing antimicrobial pharmaceutical compositions comprising the refined Ceftizoxime sodium according to a purification method of the present invention and a pharmaceutically acceptable excipient for treating infections induced by sensitive bacteria, such as lower respiratory tract infections, urinary tract infections, Abdominal infections, pelvic infections, septicemia, skin and soft tissue infections, bone and joint infections, meningitis and uncomplicated gonorrhea caused by *Streptococcus pneumoniae* or *Haemophilus influenzae* and so on. Preferably, the pharmaceutical composition can be in freeze-dried powder or in an injectable preparation.

The present invention also provides the use of the above pharmaceutical composition in the manufacture of a medicament for the treatment of infections induced by sensitive bacteria, such as lower respiratory tract infections, urinary tract infections, Abdominal infections, pelvic infections, septicemia, skin and soft tissue infections, bone and joint infections, meningitis and uncomplicated gonorrhea caused by *Streptococcus pneumoniae* or *Haemophilus influenzae* and so on. Preferably, the above infections include pneumonia, bronchitis, biliary tract infections, peritonitis, and urinary tract infections.

The present invention fundamentally changes the low-purity status of raw Ceftizoxime sodium all over the world, addresses the challenge crude Ceftizoxime sodium and Active Pharmaceutical Ingredients of Ceftizoxime sodium facing, improves a series of clinical adverse reactions caused by insoluble particles or polymer impurities, improves the quality of finished products, and reduces toxic side effects.

The method of the present invention also has advantages such as simpleness, control easiness, and easiness for industrial production.

The following examples further illustrate the invention. These examples are for the purpose of illustration and are not to be construed as a limitation upon the following appended claims.

I. HPLC Determination of the Ceftizoxime Sodium Purity:

Apparatus and Reagent: Agilent1100 Type high performance liquid chromatographer. Acetonitrile is chromatographic grade. Ceftizoxime sodium control sample (China pharmaceutical biological preparation detection department); Injection Ceftizoxime sodium powder ampoule (producted by Haerbin group medicine pharmacy general factory, Scale 1.0 g); Ceftizoxime sodium sample obtained according to a purification method of the present invention.

Chromatographic Conditions: Octadecylsilane-bonded silica as fillers; a pH 3.6 buffer (0.42 g of citric acid and 3 g of $Na_2HPO_4.12H_2O$ are dissolved in water, and then diluted to 1000 mL)—acetonitrile (9:1) as mobile phase with a detection wavelength at 254 nm. The theoretical plates calculated according to Ceftizoxime peak should be no less than 2000.

Detailed Procedures: proper amount of Ceftizoxime sodium sample is accurately measured, dissolved in water and diluted into a solution of about 64 g/mL. After shaking, 20 mL of the solution is injected into the liquid chromatograph and the chromatogram is recorded. Another proper amount of Ceftizoxime control sample, after being dissolved in 2 mL phosphate buffer (take 39.0 mL of 0.2 mol/L sodium dihydrogen phosphate solution and mix with 61.0 mL of 0.2 mol/L disodium hydrogen phosphate solution, pH value of 7.0), is determined using the same method. The content of Ceftizoxime in samples can be calculated by external standard method using peak area. Based on anhydrous material, the content of Ceftizoxime should be no less than 85.0%, with a maximum Ceftizoxime content of 94.33%.

EXAMPLE 1

10 g of Ceftizoxime sodium crude material is determined to have Ceftizoxime content of 88% by High Performance Liquid Chromatography. The crude Ceftizoxime sodium is dissolved in 200 mL water, and then the solution is extracted twice by addition of ethyl acetate with 40% volume of the aqueous solution each time. After sufficient stirring and settling for 1 hour, the organic phase is separated out to obtain the aqueous phase containing Ceftizoxime sodium.

The above mentioned aqueous phase is treated with 50 mL of 15% aqueous ammonia for 2 hours with stirring, until the pH value of the aqueous solution reaches 9-10. The precipitation is removed by filtration.

The Ceftizoxime sodium aqueous solution obtained above is warmed up to 60-70° C., to remove the remaining ammonia, and meanwhile to concentrate, until the solution volume is 120 mL. Then, 75% ethanol with a volume of 65% volume of the aqueous solution is added into the aqueous solution. Then the solution is slowly cooled down to 12° C. to recrystallize and form crystals. Ceftizoxime sodium seed crystals are introduced optionally during the cooling process. The solution is allowed to stand for 10 hours until no more crystals are formed. After centrifugation in a centrifuge and filtration, 9.0 g of white Ceftizoxime sodium is obtained after air drying, with a yield of 90%.

The $^1$H-NMR spectrum of the purified Ceftizoxime sodium prepared according to the present invention is shown in FIG. 1.

$^1$H-NMR (DMSO-d6) δ: 3.34-3.66 (2H, m), 3.84 (3H, s), 5.09 (1H, d, J=4.8 Hz), 5.81 (1H, dd, J=4.8 Hz, 8.4 Hz), 6.47-6.49 (1H, m) 6.73 (1H, s), 7.23 (2H, s), 9.61 (1H, d, J=8.4 Hz).

The Ceftizoxime content is measured as 94.10% by High Performance Liquid Chromatography (HPLC). A sample of the refined material is made into a solution of about 0.1 g/mL by adding water, and the solution is clear and colorless.

COMPARATIVE EXAMPLE 1

The crude Ceftizoxime sodium sample applied in Example 1 is purified using the purification method described in Chinese patent CN101735249A. The Ceftizoxime content is measured as 89% by High Performance Liquid Chromatography (HPLC).

EXAMPLE 2

10 g of Ceftizoxime sodium crude material prepared according to CN101671348A is determined to have Ceftizoxime content of 87% by High Performance Liquid Chromatography. The crude Ceftizoxime sodium is dissolved in 150 mL water, and then the solution is extracted three times by addition of cyclohexane with 35% volume of the aqueous solution each time. After sufficient stirring and settling for 2 hours, the organic phase is separated out to obtain the aqueous phase containing Ceftizoxime sodium.

The above mentioned aqueous phase is treated with continuous bubbling of ammonia for 2.5 hours with stirring, until the pH value of the aqueous solution reaches 8.5-9.5. Precipitation is formed and the precipitation is removed by filtration.

The Ceftizoxime sodium aqueous solution obtained above is warmed up to 55-65° C., to remove the remaining ammonia, and meanwhile to concentrate, until the solution volume is 90 mL. Then, anhydrous ethanol with a volume of 55% volume of the aqueous solution is added into the aqueous solution. Then the solution is slowly cooled down to 15° C. to recrystallize and form crystals. The solution is allowed to stand for 8 hours until no more crystals are formed. Crystals are obtained after centrifugation in a centrifuge and filtration. The mother liquid and fresh anhydrous ethanol are added together into the aqueous solution treated with ammonia, to further crystallize. 9.2 g of white Ceftizoxime sodium is obtained after washing the obtained crystals with anhydrous ethanol and drying under proper temperature, with a yield of 92%.

The Ceftizoxime content is measured as 94.2% by High Performance Liquid Chromatography (HPLC). A sample of the refined material is made into a solution of about 0.1 g/mL by adding water, and the solution is clear and colorless.

EXAMPLE 3

10 g of Ceftizoxime sodium raw material drugs (Harbin Pharmaceutical Group Pharmaceutical Factory, Batch number 20080302) with 84% Ceftizoxime content as determined by High Performance Liquid Chromatography (HPLC), is dissolved in 250 mL water. The aqueous solution is extracted four times by addition of ethyl acetate with 30% volume of the aqueous solution each time. After sufficient stirring and settling for 2 hours, the organic phase is separated out to obtain the aqueous phase containing Ceftizoxime sodium.

The above mentioned aqueous phase is treated with continuous bubbling of ammonia for 3 hours with stirring, until the pH value of the aqueous solution reaches 9-10. Precipitation is formed and the precipitation is removed by filtration.

The Ceftizoxime sodium aqueous solution obtained above is warmed up to 70-80° C., to remove the remaining ammonia, and meanwhile to concentrate, until the solution volume is 150 mL. Then 90% ethanol with a volume of 60% volume of the aqueous solution is added into the aqueous solution. Then the solution is slowly cooled down to 15° C. to recrystallize and form crystals. The solution is allowed to stand for 8 hours until no more crystals are formed. After centrifugation in a centrifuge and filtration, the filtrate and fresh 90% ethanol are added together into the aqueous solution obtained in step 2), to further crystallize. 8.9 g of white Ceftizoxime sodium is obtained after air-drying of the obtained crystals, with a yield of 89%.

The Ceftizoxime content is measured as 94.1% by High Performance Liquid Chromatography (HPLC). A sample of the refined material is made into a solution of about 0.1 g/mL by adding water, and the solution is clear and colorless.

EXAMPLE 4

10 g of expired Ceftizoxime sodium crude material is determined to have Ceftizoxime content of 80% by High Performance Liquid Chromatography. The crude Ceftizoxime sodium is dissolved in 300 mL water, and then the solution is extracted four times by addition of cyclohexane with 25% volume of the aqueous solution each time. After sufficient stirring and settling for 6 hours, the organic phase is separated out to obtain the aqueous phase containing Ceftizoxime sodium.

The above mentioned aqueous phase is treated with 50 mL 20% ammonia for 5 hours with stirring, until the pH value of the aqueous solution reaches 10-11. Precipitation is formed and the precipitation is removed by filtration.

The Ceftizoxime sodium aqueous solution obtained above is warmed up to 80-90° C., to remove the remaining ammonia, and meanwhile to concentrate, until the solution volume is 180 mL. Then 95% ethanol with a volume of 55% volume of the aqueous solution is added into the aqueous solution. Then the solution is slowly cooled down to 13° C. to recrystallize and form crystals. Ceftizoxime sodium seed crystals are introduced optionally during the cooling process. The solution is allowed to stand for 10 hours until no more crystals are formed. Crystals are obtained after centrifugation in a centrifuge and filtration. The mother liquid and fresh 95% ethanol are added together into the aqueous solution treated with ammonia, to further crystallize. 8.4 g of white Ceftizoxime sodium is obtained after washing the obtained crystals with 95% ethanol and drying under 50° C.

The Ceftizoxime content is measured as 94.25% by High Performance Liquid Chromatography (HPLC). A sample of the refined material is made into a solution of about 0.1 g/mL by adding water, and the solution is clear and colorless.

The present invention has been already illustrated according to the above examples. The foregoing examples are only intended to exemplify the present invention. It will be appreciated that numerous modifications and embodiments may be devised by the skilled in the art without deviating the spirit and essence of the present invention. Such modifications are also understood to fall within the protective scope of the present invention.

What is claimed is:

1. A process for refining Ceftizoxime sodium compound comprises the following steps:
   1) dissolving crude Ceftizoxime sodium into water, extracting from several minutes to 10 hours with cyclohexane or ethyl acetate, then separating the organic phase that contains impurities and an aqueous phase that contains Ceftizoxime sodium;

2) adding ammonia or ammonium hydroxide into the aqueous phase of step 1), stirring from several minutes to 8 hours, filtrating the precipitate, yielding an aqueous filtrate that contains Ceftizoxime sodium, and optionally, removing the ammonia in the aqueous filtrate by heating;

3) adding an alcoholic solvent into the aqueous solution of step 2), and recrystallizing by adjusting the temperature, centrifuging, washing the resultant crystals, drying and yielding the refined Ceftizoxime sodium;

4) optionally, recycling the remaining liquid of step 3) for the recrystallization as step 3).

2. The process for refining Ceftizoxime sodium according to claim 1, wherein the volume of cyclohexane or ethyl acetate in step 1) is between 10% and 50% of the volume of the Ceftizoxime sodium aqueous solution; repeating the extraction for three times.

3. The process for refining Ceftizoxime sodium according to claim 1, wherein the time each extraction in step 1) is between 1 and 6 hours.

4. The process for refining Ceftizoxime sodium according to claim 2, wherein the time each extraction in step 1) is between 1 and 6 hours.

5. The process for refining Ceftizoxime sodium according to claims 1, wherein the stirring is conducted in step 1) for efficient extraction before the phase separation.

6. The process for refining Ceftizoxime sodium according to claim 1, characterized in that, in step 2) ammonia is continuously passed through or 15-25% ammonium hydroxide is added into the aqueous phase obtained in step 1).

7. The process for refining Ceftizoxime sodium according to claim 1, characterized in that, the time of stirring in step 2) is between 1 and 5 hours until the pH value of the aqueous solution reaches at the range between 9 and 10.

8. The process for refining Ceftizoxime sodium according to claim 1, characterized in that, the aqueous solution is heated up to the temperature between 50 and 80° C. after filtrating the precipitate in step 2).

9. The process for refining Ceftizoxime sodium according to claim 1, characterized in that, the temperature in the step 3) is adjusted between 50 and 80° C.; the Ceftizoxime sodium aqueous solution obtained in step 2) is concentrated to decrease the ratio of water by adding from 75% to 100% of ethanol into the aqueous solution up to 50-70% volume of the aqueous solution;

the resultant solution is cooled down to the temperature between 10 and 12° C.

10. The process for refining Ceftizoxime sodium according to claim 9, characterized in that, Ceftizoxime sodium seed crystals are optionally introduced during the cooling process.

11. The process for refining Ceftizoxime sodium according to claims 1, wherein the solution obtained in step 3) by cooling down to the temperature between 10 and 12° C. is recycled to step 3) by adding the solution with the alcoholic solvent into the aqueous solution obtained in step 2).

\* \* \* \* \*